United States Patent [19]

Walcott et al.

[11] Patent Number: 4,823,072

[45] Date of Patent: Apr. 18, 1989

[54] MEASUREMENT OF THE POLARIZED POTENTIAL OF BURIED PIPELINE HAVING IMPRESSED CURRENT CATHODIC PROTECTION

[76] Inventors: Kenneth J. Walcott, 6670 Statesboro Rd., Dayton, Ohio 43204; Neil G. Thompson, 7849 Spirowood St., Dublin, Ohio 43017; George T. Ruck, 6812 Bowerman St., W., Worthington, Ohio 43085; Steven B. Helton, 1849 N.W. Ct., Apt. B, Columbus, Ohio 43212

[21] Appl. No.: 43,040

[22] Filed: Apr. 27, 1987

Related U.S. Application Data

[63] Continuation-in-part of Ser. No. 904,098, Sep. 4, 1986, abandoned.

[51] Int. Cl.$^4$ .............................................. G01R 27/20
[52] U.S. Cl. ................................ 324/65 CR; 204/196; 204/404; 307/95
[58] Field of Search ............... 204/1 C, 1 T, 196, 147, 204/404; 307/95; 324/71.1, 71.2, 65 CR, 425, 439

[56] References Cited

U.S. PATENT DOCUMENTS

| | | | |
|---|---|---|---|
| 4,160,171 | 7/1979 | Merrick | 307/95 |
| 4,383,900 | 5/1983 | Garrett | 204/147 |
| 4,664,764 | 5/1987 | Zofan | 204/147 |

Primary Examiner—A. D. Pellinen
Assistant Examiner—H. L. Williams

[57] ABSTRACT

A method for detecting the polarized potential of a buried pipe which is cathodically protected by rectified alternating current impressed upon the pipe. Each rectified protection current is periodically pulsed to an off state for a precise pulse duration and pulse period which are integral multiples of the period of the alternating current. The potential between the pipe and a reference electrode at the test site is sampled and analyzed to detect the polarized potential. It is analyzed to find the area under the portion of the waveform during which no off pulses are present and to use that area to detect the on potential. The area within the off pulses, after reactive spikes are eliminated, is substracted from the on potential area to determine the IR drop potential. The IR drop potential is then subtracted from the on potential and the difference is displayed as the polarized potential.

16 Claims, 7 Drawing Sheets

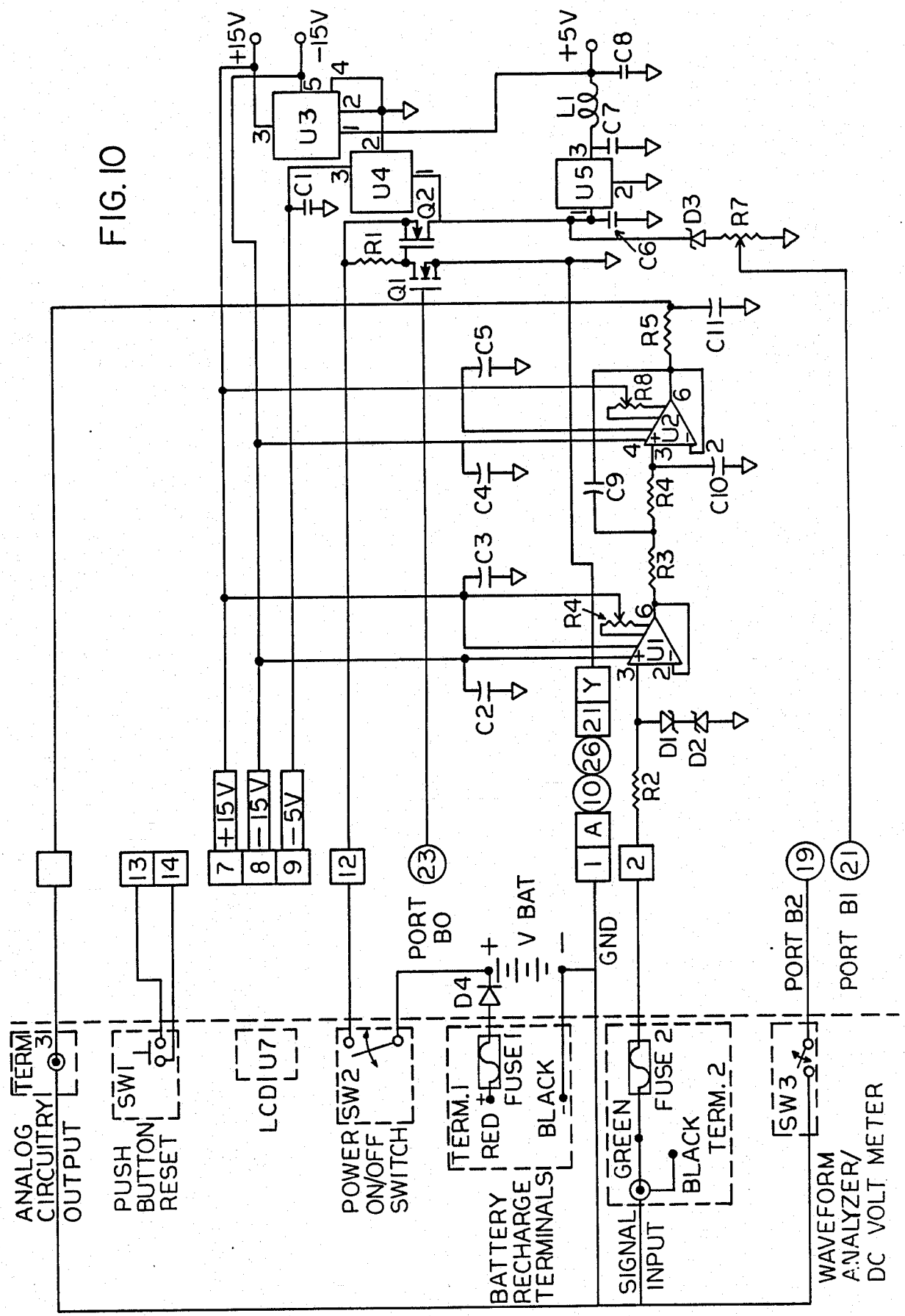

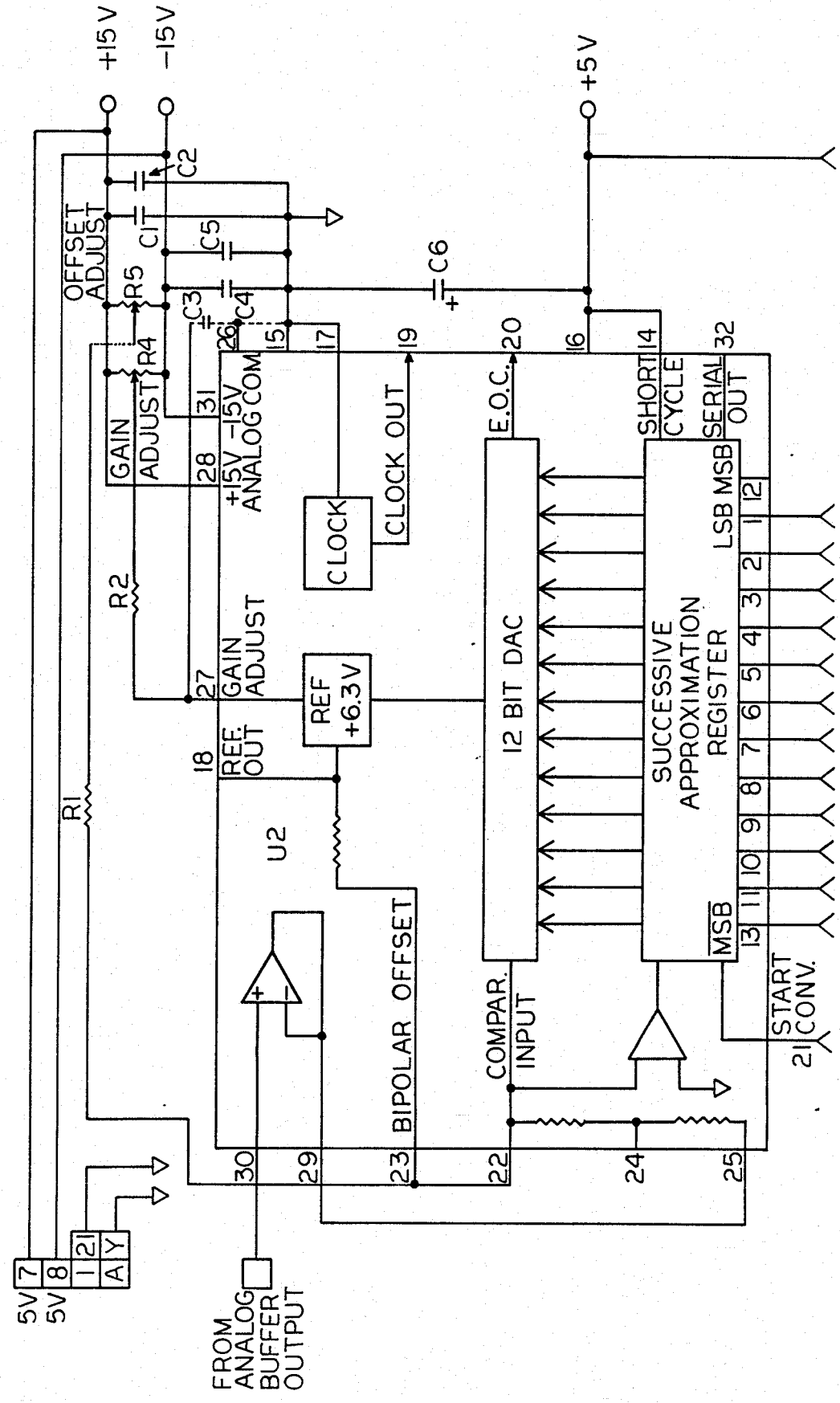
FIG. IIA

MEASUREMENT OF THE POLARIZED POTENTIAL OF BURIED PIPELINE HAVING IMPRESSED CURRENT CATHODIC PROTECTION

TECHNICAL FIELD

This application is a continuation-in-part of our co-pending application Ser. No. 904,098 filed Sept. 4, 1986, now abandoned.

This invention relates generally to the detection of the polarized potential of a pipe protected by an impressed, rectified alternating current, protection system and more particularly relates to such a system for detecting the polarized potential by analysis of pipeline to buried electrode potential waveforms at a test site along the pipeline without any need for synchronizing the switching times of the protection circuits and yet in a manner which permits the polarized potential to be measured where the test site is affected by multiple protection systems.

BACKGROUND ART

Buried structures, particularly metallic structures such as a gas pipeline, undergo a corrosion process due to the galvanic activity at the interface between the surface of the pipe and the surrounding soil. If the potential is measured between the pipe and a second buried electrode, a naturally occurring battery will be observed with the soil forming the electrolyte.

A copper electrode having a copper sulfate surface is widely adopted as a standard reference electrode for measuring the potential between a buried electrode and a pipeline for determining the level of pipeline corrosion protection. A natural, freely corroding steel surface will typically show a free corrosion potential between such a standard reference electrode and the pipe in the range −0.62 volts to −0.68 volts.

A common method of retarding the corrosion is to impress a current through the soil to the pipe from an external, rectified alternating current source which opposes the current of the corrosion process. This makes the pipe the cathode of the resulting galvanic cell and therefore prevents or at least mitigates corrosion on the buried pipeline. During cathodic protection, the impressed current increases the cathodic, or reduction reaction on the pipeline surface while simultaneously decreasing the corrosion or oxidation reaction. Cathodic protection is applied by an impressed current cathodic protection system which typically uses a rectifier to apply an average DC cathodic current to a pipeline by connecting the pipeline to the negative terminal of the rectifier output and an inert buried anode to the positive terminal.

Criteria have been established to measure the effectiveness of the impressed current cathodic protection system. One important criterion is the measurement of the polarized potential of the pipeline using the standard copper/copper sulfate reference electrode. The measured polarized potential is the difference in the potentials of the pipe and the reference electrode in the soil electrolyte while in their protected state. This is the most commonly used criterion and provides that corrosion is assumed sufficiently mitigated when the polarized potential between a steel pipe and the standard reference electrode is −0.85 volts. That is, when the polarized potential at the pipe is −0.85 volts with respect to the standard reference electrode, the pipe is considered properly protected.

A variety of problems exist, however, with attempts to measure this polarized potential. First, as recognized in U.S. Pat. No. 4,591,792, the impressed protection system within the soil. Thus, the polarized potential, while the protection current is impressed, cannot be directly measured. Instead, while the current is impressed, the potential measured between the reference electrode and the pipe is the algebraic sum of the polarized potential and the IR drop in the soil between the pipe and the reference electrode.

One solution to this IR drop problem, which has been commonly used, is to interrupt the impressed protection current and measure the potential between the pipe and the reference electrode during the interruption interval. The theory is that such interruption will eliminate the IR drop in the soil and thus permit direct measurement of the polarized potential.

One problem with such interruption systems arises from the fact that a pipeline is ordinarily protected by a series of discrete protection circuits spaced along the length of the pipeline. Therefore, the potential measured at a test site between the pipeline and a reference electrode includes the sum of the pipe to reference electrode IR drops contributed by each of the protection circuits. Thus, for the interruption system to work, the interruption must be synchronized so that all interruptions occur simultaneously.

Although synchronization is expensive, it is currently used on some protection systems to facilitate the measurement of the polarized potential. However, further problems exist which are not addressed by such synchronization systems. A long pipeline behaves electrically as an inductor. That inductive property, together with other reactive circuit elements, create exponentially decaying transients or spikes when the current of such systems is switched. In particular, immediately after the impressed protection current is switched off, and again immediately after it is switched back on, a transient spike is created which requires a finite interval of time to decay. Thus, the interruption of the impressed protection current does not result in an immediate drop of the potential between the pipe and the standard electrode to the polarized potential. Instead, the potential drops further by an amount of an inductive spike resulting from the collapse of the magnetic field about the pipe as its energy is returned into the circuit. The result is that the potential between the pipe and the standard electrode, immediately after interruption, is not the polarized potential, but rather is the sum of the polarized potential and this inductive spike. Only after the inductive spike has decayed will the potential between the pipe and the standard electrode reach the polarized potential.

Still another problem with interruption systems is that after the protection current is interrupted and after the transient decays, the pipe interface begins to depolarize as the system begins to electrochemically revert back to its natural battery operation. Thus, the potential measured between the reference electrode and the pipe begins to return from the polarized potential at which the pipeline is protected to its free corrosion potential. Therefore, after a substantial time has elapsed, the potential between the pipe and the standard electrode will no longer be the polarized potential.

This latter problem is aggravated by the fact that currently used metering devices, such as a strip chart or a galvanometer-type meter, have a substantial, mechanical inertia associated with them. As a result, they require a substantial period of time until they can react to a change in potential. The response time of such devices is ordinarily sufficiently long that some reversion of the potential toward the free corrosion potential has occurred before a steady state reading is obtained. In fact, the response time of strip charts and galvanometers is so slow that they will not indicate the inductive spike and will settle to a steady state only after some reversion of the potential between the pipe and the standard electrode from the polarized potential toward the free corrosion potential. It thus becomes a matter of art and interpretation and consequent inaccuracy to determine from these devices the actual polarized potential.

Finally, yet another problem which exists in all of these systems is the problem of the presence of noise or unwanted signals in the form of alternating currents in the soil even after the interruption of protection circuits. These noise currents are in the form of 50 Hz or 60 Hz currents which have been picked up from electrical equipment in the region and some RF noise.

Therefore, it is an object and feature of the present invention to eliminate any need for synchronizing the switching off of multiple spaced protection circuits distributed along the pipeline, to eliminate the problems which arise from such extraneous alternating current noise signals and to obtain a reliable measurement of the polarized potential $E_{OFF}$ after the reactive spike has decayed but before the potential makes any substantial reversion from the polarized potential which exists during operation of the protection system toward the free corrosion potential.

BRIEF DISCLOSURE OF INVENTION

In the present invention a pulse generator is permanently installed in each rectifier protection circuit and periodically pulses the rectified current to an off state. However, the timing of the off pulse for each of a series of protection circuits spaced along a pipeline does not need to be synchronized so that the pulses would occur simultaneously or in any particular relationship. Instead the off pulses occur substantially randomly where there are multiple protection circuits. The pulse duration of each protection circuit is identical and the pulse period of each protection circuit is identical. Both are timed by, and preferably are integral multiples of, the period of the 50 Hz or 60 Hz electrical energy distribution system so that the pulse width and pulse duration vary in proportion to the ordinary, minor variations in the period of the nominal 50 Hz or 60 Hz power source.

The pulse duration is selected so that it is longer than the time for the reactive transients to decay, but shorter than the time for substantial variations in the polarized potential toward the free corrosion potential to occur.

The potential between the pipe and the reference electrode is detected and converted to digital samples. If a single protection circuit affects the test site, sampling may be confined to the off pulse. However, where multiple protection circuits affect the test site potential, sampling is done over the entire pulse period and because this also operates when there is a single protection circuit, in practice sampling is preferred over the entire pulse period to provide universal applicability. The digital samples are a set of an integral number of samples taken during each period of the rectified alternating current, usually 50 Hz or 60 Hz. Each set of samples is taken with the same phase relationship to the alternating current as the other sets of samples are taken. When a single protection circuit affects the test area, digital waveform analysis is then utilized to detect from the samples the polarized potential by detecting the potential between the pipe and the standard electrode during the portion of the off pulse after the transients have substantially decayed.

Where multiple protection current sources substantially affect a test site, the pulse period must be greater than the product of the maximum number of impressed current sources which substantially affect the test site multiplied by the sum of the pulse duration and the transient decay time after the off pulse in order to assure that there will be some interval during any entire pulse period during which there are no pulses or transients regardless of the phase relationship between the pulse cycles from the different protection circuits. With multiple protection circuits the average is detected of the potentials between the pipe and the buried standard electrode during all the off pulse portions which are after the reactive transients have decayed. This average is the net polarized potential which results from the distributed currents from all of the protection circuits which affect the pipe at the test site.

BRIEF DESCRIPTION OF DRAWINGS

FIG. 10 and FIG. 11 are schematic diagrams illustrating hardware embodying the present invention.

Figure 1:
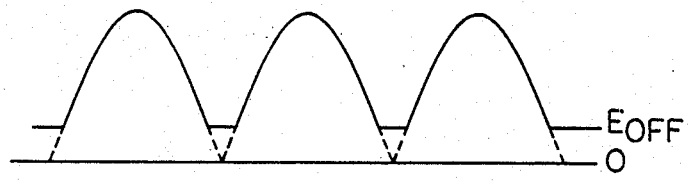
FIG. 1 is an oscillogram of the potential waveform observed between a pipe and a standard electrode when no reactive spikes are present.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

FIG. 1 illustrates an ideal time-varying pipe to electrode potential for a typical protection system where no reactive spikes exist. It illustrates a conventional, full wave rectified sine wave as extended by the dashed lines to the horizontal zero axis. With no reactive transients, a flat spot appears between the rectified wave lobes. The diodes of the rectifier interrupt the current or in the past were assumed to interrupt the current when the rectifier output potential became less than the polarized potential. The flat spots occur at the polarized potential and thus at the time interval during which protective current ceases during each cycle. As described in U.S. Pat. No. 4,591,792, the potential at these flat regions can be detected and represents the polarized potential $E_{OFF}$.

However, field testing in some environments has indicated that a transient spike is often present. For example, in FIG. 2(a) such an exponentially decaying spike is illustrated where its time constant is sufficiently short that it can entirely decay during the brief nonconducting portion represented by the flat spots in FIG. 1.

Figure 2:
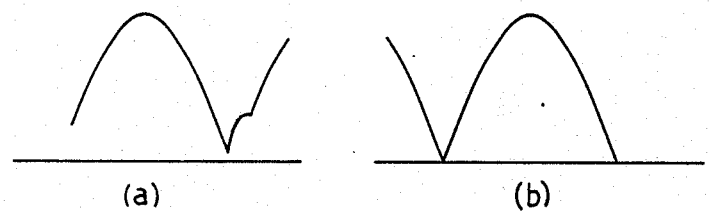
FIG. 2 is an oscillogram including part a which illustrates a waveform like that of FIG. 1, but in which relatively short duration reactive spikes are present and in FIG. 2b in which reactive spikes of longer duration are present.

Unfortunately, however, often the transient does not decay within that brief interval and instead the current appears as shown in FIG. 2(b). In this situation the transient spike causes current to flow, as a result of the pipe inductance, during the entirety of the brief interval during which the rectifier output potential of the protective circuit is less than the polarized potential. As a result, no detectable flat region in the potential waveform exists. The spike can even extend below the zero potential axis causing a brief reversing potential.

In accordance with the present invention, a switching means or pulse generator is interposed in the protection circuit either between the rectifier and the protection system anode or between the rectifier and the pipe. This switching means periodically pulses the rectified current to an off state.

Figure 3:
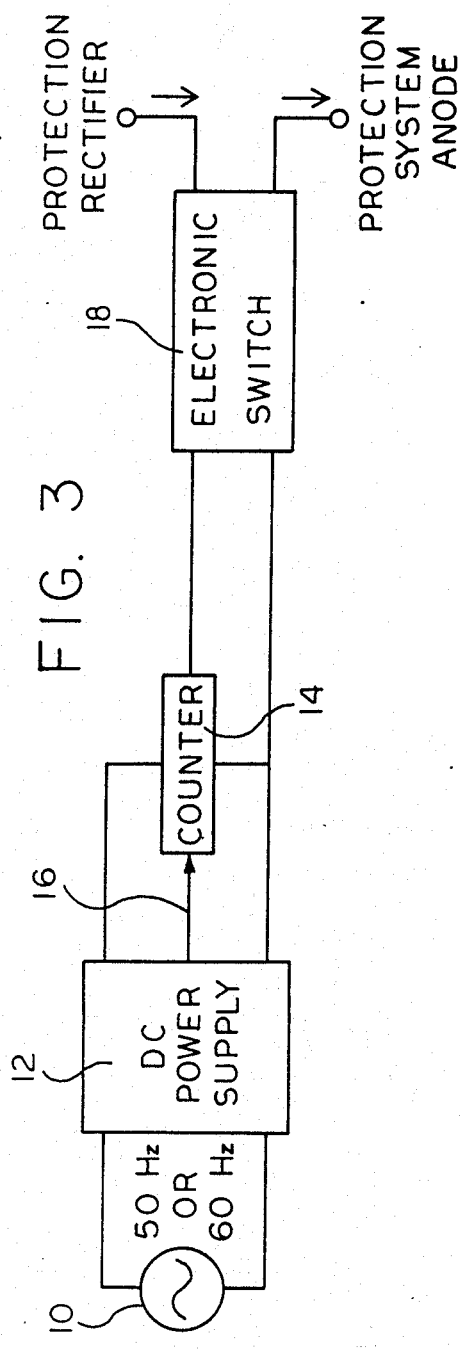
FIG. 3 is a block diagram of a pulse generator circuit used in embodiments of the present invention.

As illustrated in FIG. 3, the conventional 50 Hz or 60 Hz source 10 is rectified by a power supply 12 to operate a counter 14. The counter 14 counts pulses of the alternating current from an input 16. After counting a selected number of such pulses, the electronic switch 18 is turned on and, after another selected number of such pulses, is then turned off. Preferably, the off pulse duration is equal to an integral multiple of the period of the alternating current source 10 and the pulse period is also equal to an integral multiple of the period of the alternating source 10. In this manner the pulse duration and the pulse period are timed with the alternating current source 10 so that both the pulse duration and period vary in proportion to variations in the period of the alternating current.

The pulse duration which is selected for the off pulses is selected so that it is longer than the time required for the reactive switching transients to decay, but shorter than the time for the polarized potential to vary substantially, that is before the polarized potential makes any substantial reversion toward the free corrosion potential. In the preferred embodiment, the pulse duration is equal to 16 alternating current periods which, for 60 Hz, is slightly over a quarter of a second.

Where a pipeline is protected by a series of protection circuits spaced along the pipeline, each protection circuit is provided with such a switching means, for example of the type illustrated in FIG. 3. The protection current at each such protection circuit is pulsed off by a pulse of the same duration and period as the off pulse at all other protection circuits. However, the relative timing or phase relationship between these off pulses is not synchronized and therefore the switching means are free running and the pulses occur at substantially random, relative times.

The pulse period is selected so that it is greater than the product of the maximum number of impressed current sources which substantially affect a test site at a buried electrode along the pipe multiplied by the sum of the pulse duration and the transient decay time immediately following the off pulse. In the preferred embodiment, the pulse duration was selected to be approximately two to three times the transient decay time. Therefore, the pulse period should be greater than about 1.5 times the pulse duration times the number of protection circuits. The preferred embodiment is designed for 6 protection circuits so we chose 4.25 seconds or more specifically, for ease of digital calculation, we chose 256 alternating current periods. This is done so that regardless of the phase relationship between the pulses from the different protection circuits, there will always be some interval during any pulse period during which no pulses or subsequent transients are present between the pipe and a test electrode.

The preferred embodiment, for example, which has been constructed assumes that six protection circuits are the most which will substantially affect any one test site.

Since each protection circuit is switched off by the pulse generator for only about a quarter of a second out of each 4.25 seconds, the presence of the pulse has no significant influence on the level of polarization and therefore the level of protection applied to the pipe. Because of this fact and the fact that the pulse generator is relatively inexpensive, it can be permanently mounted as a part of each protection rectifier.

Figure 4:
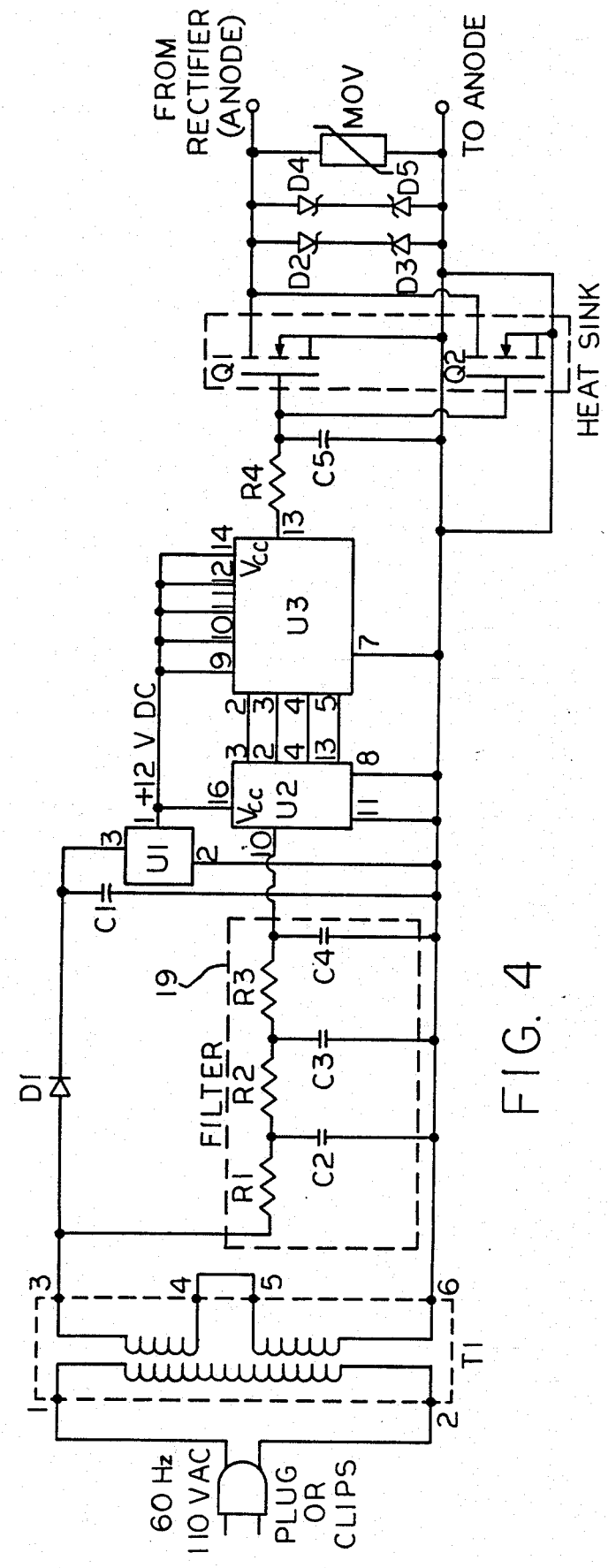
FIG. 4 is a detailed schematic diagram of the pulse generator of FIG. 3.

The detailed schematic diagram of the pulse circuit is illustrated in detail in FIG. 4. A power MOSFET Q1 and Q2 switches the rectifier output current on and off to generate the zero current pulses. MOSFETS used in the prototype were types MTM40N20 and MTM15N20.

The counter circuitry controls the zero current pulse width or duration and the zero current pulse cycle time or period. It consists of a filter circuit 19, a 14 bit counter U2, and a NAND gate U3. The counter U2 generates its timing from the 60 Hz power lines. The input filter 19 is used to suppress any transients present on the power lines. The filter output is input to the clock input of the 14 bit counter U2 IC chip. Selected output bits are input to the 8 input NAND gate U3 to achieve the desired timing. The output of the NAND gate drives the power MOSFET Q1, Q2.

The DC supply circuitry contains a transformer T1, a diode D1, a capacitor C1, and a 12 volt DC linear regulator U1. The transformer charges the capacitor C1 through the diode D1 and also supplies the 60 Hz signal for counting to the counter circuitry filter R1, R2, R3, C3 and C4 to the counter U2.

Figure 5:
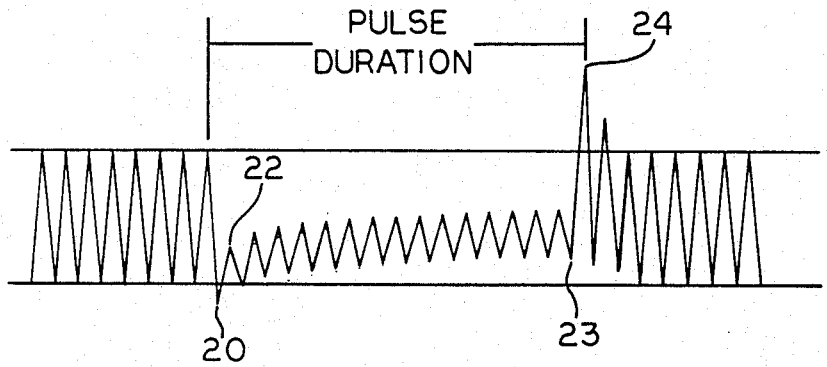
FIG. 5 is an oscillogram illustrating the potential observed between the pipe and a standard electrode during an off pulse.

An oscillogram illustrating the result of pulsing the rectified current in accordance with the present invention is shown in FIG. 5. The figure shows only a portion of a pulse period, but many 60 Hz periods. It shows that prior to time 20, the full wave rectified alternating current protection potential is present between the pipe and the reference electrode. However, at the time 20 the protection circuit is switched off by the pulse generating switch means and a transient 22 occurs. After the transient settles, but before the end 23 of the pulse duration, alternating current signals are still present in the form of noise and/or rectifier currents from more remote protection circuits. At time 23 the pulse ends and the protection current is switched on causing a transient or spike 24, after which the circuit settles back to a steady state condition.

Conventional analog to digital conversion techniques utilizing known sampling concepts are used to sample the waveform illustrated in FIG. 5 and convert it to digital samples. The sampling circuitry is timed by the alternating current power signal of 50 Hz or 60 Hz which is the same signal available at the protection circuits. The same quantity or number of integral digital samples are taken during each period of the alternating current. In the preferred embodiment, 64 samples are taken during each 50 Hz or 60 Hz cycle. Each set of samples has the same phase relationship to the alternating current as every other set of samples. Thus, while the time or angle relative to the zero crossover of the alternating current at which the samples begin is not critical, it is important that all samples begin at substantially the same time or phase relationship to the alternating current.

In the event that a single protection circuit is affecting the test site, the samples are taken at least during the interval of the pulse duration, but preferably and in the event that multiple protection circuits affect the test site, the sampling is done over an interval of time which equals a pulse period of approximately 4.25 seconds in the preferred embodiment.

These digital samples for a pulse period are then digitally filtered to eliminate alternating current signals. This is done by summing all the samples, 64 in the preferred embodiment, for each 50 Hz or 60 Hz cycle to form a composite sample for each 50 Hz or 60 Hz cycle. Each composite sample thus represents an average of the signal during one alternating current period and also represents the area under a graph of the waveform for one alternating current period.

Figure 6:
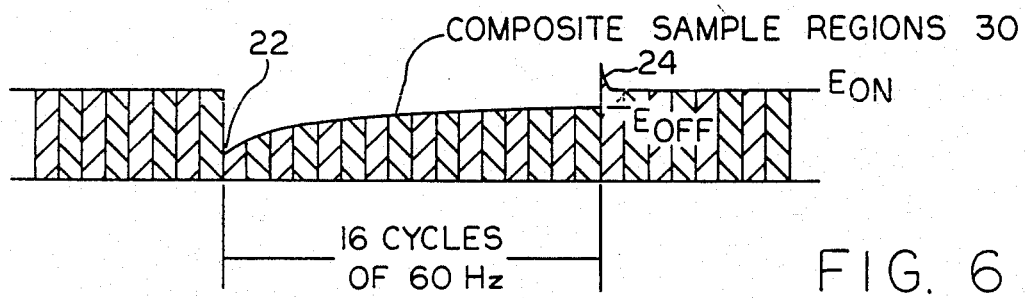
FIG. 6 is an oscillogram illustrating the waveform of FIG. 5 after filtering out alternating currents.

FIG. 6 illustrates the waveform after filtering of the alternating components and illustrates the composite sample regions 30. It shows the spike 22 and spike 24 after filtering of alternating potentials.

Other analogous modes of operation can be used in which each composite sample can be averaged with corresponding composite samples during subsequent periods, thus giving a result which is less dependent upon any effects of random noise or time variations at considerably lower frequencies than the alternating current of 50 Hz or 60 Hz.

FIG. 6 also shows the potential $E_{ON}$ which represents the average or DC potential between the pipe and the reference electrode during the application of the protective current. Also apparent is the potential $E_{OFF}$ which is the potential after the decay of the transient 22 and therefore is the polarized potential which an instrument embodying the present invention seeks to detect.

The result of this summation of the 64 samples for each cycle of alternating current will, in the preferred embodiment, provide 256 averaged composite samples for the detected pulse period over which samples are taken. The time over which samples are taken is equal to a pulse period and therefore must include at least one complete pulse from each protection circuit which affects the test site. The problem then is to determine the $E_{OFF}$ potential which is the potential during the off pulse after the transient has decayed or, in the case of multiple protection circuits, is the average of the $E_{OFF}$ levels from all off pulses during the portion of the pulses after which the transients have decayed.

This level is found by processing the samples in a manner which finds certain areas under the waveform by summing the samples as a digital integration process. These areas can then be divided by the number of pulses which are summed in the integration which represents the time over which the integration occurs to find an average potential over that time interval.

The $E_{ON}$ potential is found essentially by first finding the area under portions of the waveform at which no off pulse wells are present. This is accomplished by looking at the 256 composite samples which represent one entire pulse period. The smallest M composite samples are discarded where M is at least the product of the number of alternating current cycles in a pulse duration multiplied by the maximum number of impressed current protection sources which substantially affect a test site. For example, in the preferred embodiment 96 of the 256 composite samples are discarded. The 96 represents 16 times 6. In effect, this discards those smallest samples which must include all of the samples taken during off pulses.

Of the remaining 160 samples the largest N samples are then discarded. N is at least the product of the integral number of alternating current cycles which occur during the reactive switching transient decay which follows the off pulse multiplied by the maximum number of impressed current sources affecting the test site. This eliminates those samples which were taken during the transient spikes, such as transient spike 24, which occur after the off pulses. In the preferred embodiment N was chosen as 32. This leaves 128 composite samples which necessarily were taken when no off pulses were present at the test site from any protection circuit. Since these samples represent the integral of, or area under, one-half of a pulse period, their sum may be subsequently divided by 128 to arrive at the potential $E_{ON}$.

Figure 7:
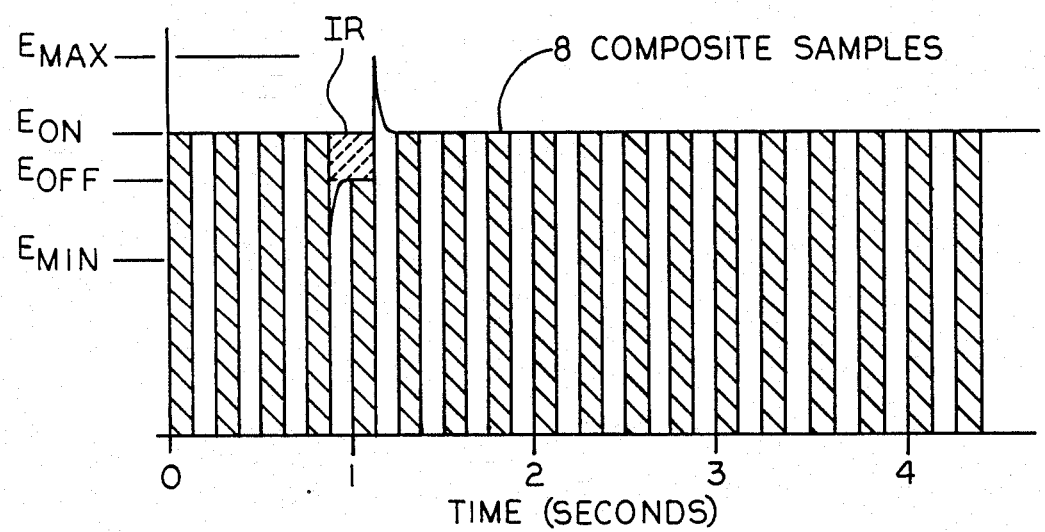
FIG. 7 is an oscillogram like FIG. 6 illustrating the comb in operation of the present invention.
Figure 8:
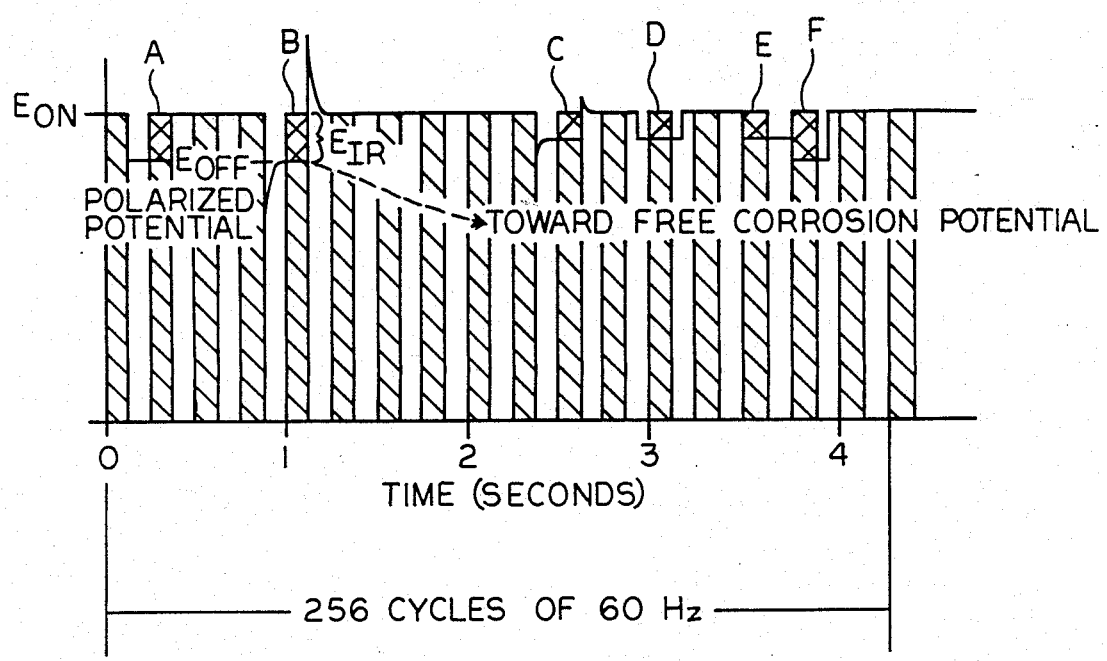
FIG. 8 is an oscillogram similar to that of FIG. 7 illustrating several pulses.

The potential difference $E_{IR}$ between $E_{ON}$ and the polarized potential $E_{OFF}$ is then obtained by first performing an eight point sieve on the data set of 256 composite samples. This is illustrated in FIGS. 7 and 8. To perform the sieve, a series of sieves or combs of digital data are formed and the largest comb is selected as representing the area beneath the waveform with all off pulse wells present, but with the spikes all removed.

As a first step, illustrated in FIG. 7, a first comb is formed by summing together the first eight composite samples, ignoring the 9th through the 16th samples, summing the 17th through the 24th sample and so forth summing alternate sets of 8 samples with intermediate eight sample regions which are ignored. Thus, each tooth of the comb represents the sum of eight composite samples and these sums representing each tooth are then summed together to provide a single sum representing the entire comb or sieve which is a sum of 128 composite samples.

The second comb is then formed by advancing one composite sample and repeating the process. Thus, the second comb is obtained by summing the 2nd through the 17th sample, skipping the 18th through the 25th sample and so forth repeating the process until a second set of 128 samples is obtained. These samples are summed to provide a sum representing the second comb. This process is repeated until sums representing 16 such combs are stored in memory, each sum representing the sum of 128 samples.

The largest sum is then selected and represents the area under the waveform with spikes removed. As can be seen in FIG. 7, the illustrated comb would be the selected sum.

This conclusion is based upon the initial observation with respect to FIG. 7 that other comb sums which would include some of the transients would, at a maximum be equal to the selected comb or would be smaller.

From experimental observation, the initial spike at the beginning of an off pulse is as great as or greater than the spike after the off pulse. When the initial spike is greater, any comb sum including it would be less than one not including it.

From experimental observation, the off pulses from distant protection circuits do not produce significant spikes because the necessary high frequencies do not propagate through the earth. The remote pulses tend to be flat and therefore samples taken during them are uniform regardless of where, during their duration, the samples are taken.

This sum of 128 samples, representing the comb giving the largest sum, is then subtracted from the sum, described above, of the 128 samples which were taken when no off pulses were present at the test site from any protection circuit. The effect of this is to determine, in the case of a single off pulse system, one-half the area, designated IR in FIG. 7, in the well of the off pulse with the spikes removed.

If multiple protection circuits affect the test site so that a waveform, such as illustrated in FIG. 8, exists, the difference represents the sum total of areas A, B, C, D, E, and F of FIG. 8. This is divided by 8, which represents the eight composite samples (eight alternating current cycles) making up each tooth of the comb to give a total average IR drop for the total contribution of all protective circuits. This is the effective IR drop $E_{IR}$ in the soil for all protective circuits.

Thereafter the computed $E_{IR}$ is subtracted from the above computed $E_{ON}$ and the difference $E_{OFF}$ is displayed and is the polarized potential.

Of course, the principles of the present invention may be applied to other quantitative sampling and computing selections as desired. If more than six protection circuits affect a test site, a longer pulse period may be used or the pulse period duration and sample rate may be varied in accordance with the principles of the present invention in other ways which will be apparent to those skilled in the art.

Therefore, in summary, a waveform analyzer embodying the present invention takes data sets based on the cycle time and pulse duration of the pulse generator which in turn is based upon the cycle time of the alternating current applied to the protection circuits and the waveform analyzer. Interference in the data set, such as from the 50 Hz or 60 Hz alternating current and harmonics thereof, are suppressed by digital filtering techniques. Since the cycle time of each pulse generator is the same, the waveform analyzer will store one off pulse (IR drop area) from each rectifier affecting the test site during a data set. The total IR drop due to all rectifiers is calculated by finding the total pulse area in the data set and dividing by the pulse width (in number of data sample intervals) since the pulse width at each rectifier is the same. The total pulse area is equal to the total on potential, $E_{ON}$, area minus the total data set area. The off potential, $E_{OFF}$, is then calculated by subtracting the IR drop from the on potential, $E_{ON}$. This is illustrated in the flow chart of FIG. 9.

Figure 9:
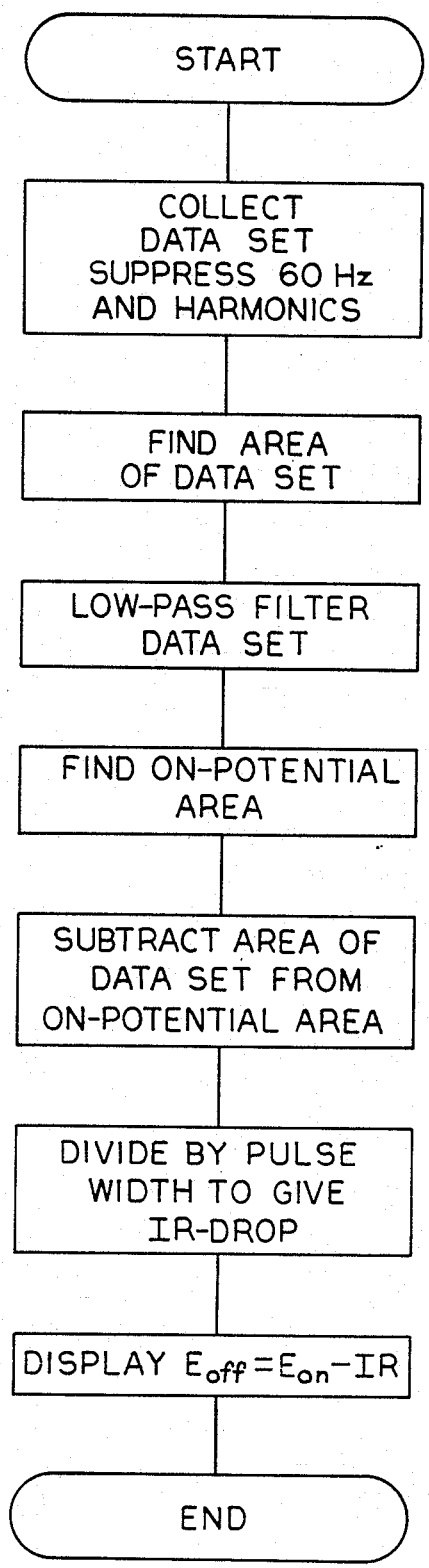
FIG. 9 is a flow chart illustrating the method of the present invention.
Figure 11B:
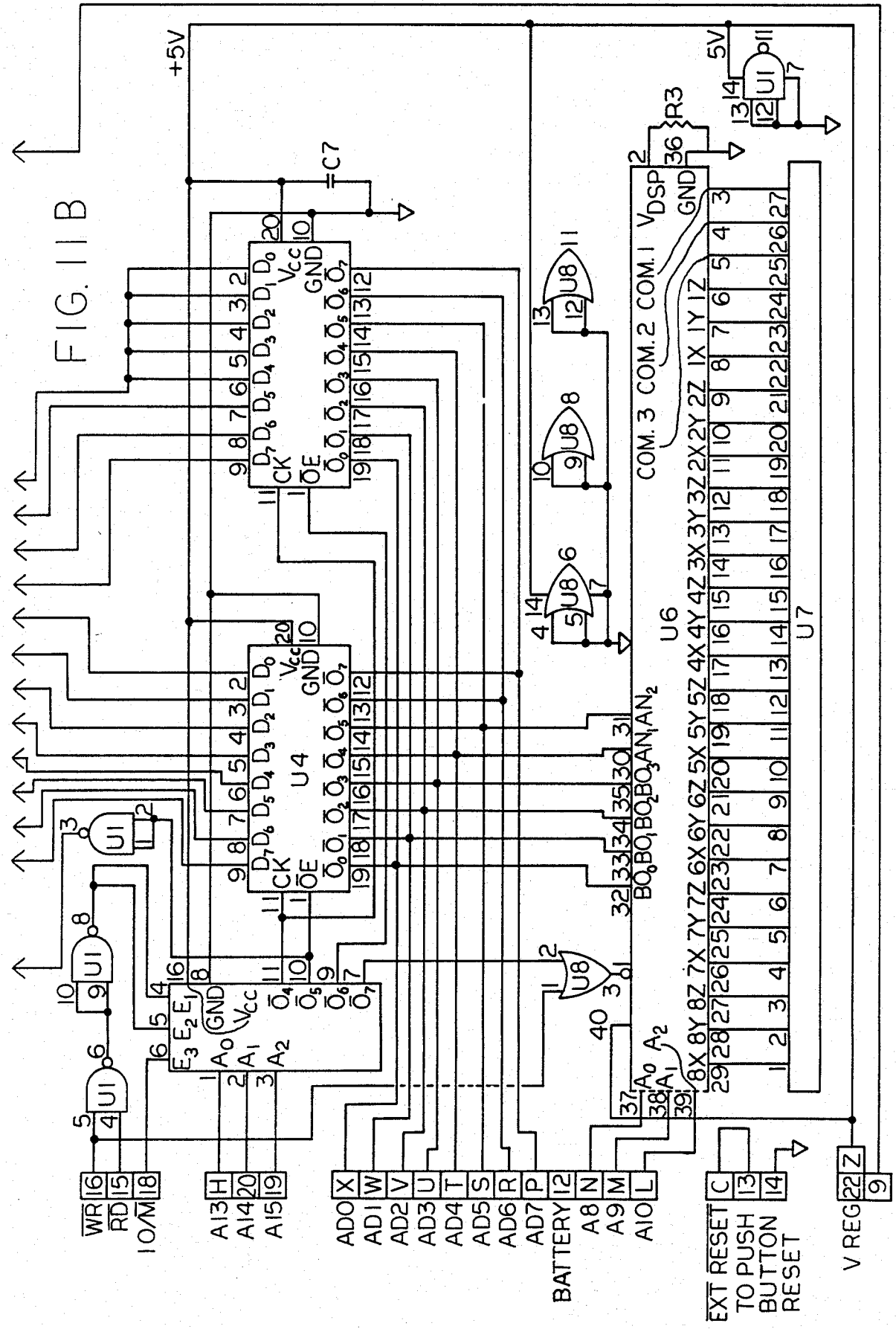

The present invention may be implemented in an infinite variety of analog to digital converter and computer hardware configurations. FIG. 9, however, illustrates a schematic diagram of a power supply and analog board which connects to the digital peripheral board of FIG. 10 and these in turn connect to a standard desk top, portable personal computer. This circuit has been implemented using a single board computer in which the CPU is a CPU-6805 manufactured by ONSET Computer Corporation that communicates with the illustrated custom circuit board through a C-44 bus backplane and a ribbon cable. The 5 MHz clock crystal was replaced with a 4.1952 MHz crystal. Because the invention does not lie in the waveform analyzer hardware itself and because a variety of hardware constructions may be used, further details of the hardware are not described.

While certain preferred embodiments of the present invention have been disclosed in detail, it is to be understood that various modifications may be adopted without departing from the spirit of the invention or scope of the following claims.

We claim:

1. A method for detecting the polarized potential of a buried pipe which is cathodically protected by rectified alternating current impressed upon a pipe by one or more rectified protection current sources, method comprising:
   (a) periodically pulsing the rectified protection current each protection current source to an off state;
   (b) sampling the potential waveform between the pipe and a reference electrode over a time interval equal to the off pulse period to collect a data set of sample signals representing said waveform;
   (c) digitally filtering the data set to remove signals at the alternating current frequency and above;
   (d) integrating sample signals of the data set during which no off pulses are present to get a first sum;
   (e) integrating sample signals along the waveform to a second sum;
   (f) subtracting the second sum from the first sum to obtain a difference which is proportional to the average IR drop $E_{IR}$ in the soil;
   (g) dividing the difference by the number of samples taken in each off pulse in order, to obtain $E_{IR}$;
   (h) diving said first sum by the number of summed samples in it to obtain potential $E_{ON}$;
   (i) subtracting $E_{IR}$ from $E_{ON}$ to obtain the polarized potential $E_{OFF}$; and
   (j) displaying the polarized potential.

2. A method for detecting the polarized potential of a buried pipe which is cathodically protected by rectified alternating current impressed upon the pipe, the method comprising:
   (a) periodically pulsing the rectified current to an off state for a off pulse duration which is longer than the time for reactive switching transients to decay and shorter than the time for the polarized potential to vary substantially, the off pulse duration and period being timed with said alternating current so that the off pulse duration and period vary in proportion to variations in the period of said alternating current;
   (b) converting the time varying potential between the pipe and a buried electrode at least during the off pulse duration to digital samples, said digital samples being a set of an integral number of samples during each period of said alternating current; and
   (c) detecting from said samples the polarized potential by detecting the potential, $E_{OFF}$, between the pipe and the buried electrode during the portion of said off pulse after said transients have substantially decayed.

3. A method for detecting the polarized potential of a buried pipe which is cathodically protected by a plurality of current sources spaced along and cathodically protecting said pipe, each source impressing a rectified alternating current upon the pipe, the current at a selected test site along the pipe being the sum of portions of currents impressed upon the pipe by more than one of said sources, the method comprising:

(a) periodically pulsing each of the impressed currents to an off state, each current being off pulsed for period of the same duration and period but at substantially random relative times, said off pulse duration being longer than the time for reactive switching transients to decay and shorter time for the polarized potential to vary substantially, the off pulse period being greater than the product of the maximum number of impressed current sources which substantially affect a test site at a buried electrode along the pipe, multiplied by the sum of the off pulse duration and the reactive switching transient decay time, the off pulse duration and period being timed with said alternating current so that the off pulse duration and period vary in proportion to variations in the period of said alternating current;

(b) converting the time varying potential between the pipe and the buried electrode to digital samples during a off pulse period, said digital samples being a set of an integral number of samples during each period of said alternating current, each set of samples having the same phase relationship to the alternating current as the other sets of samples; and (c) detecting from said samples the polarized potential by detecting the average of the potential, $E_{OFF}$, between the pipe and the buried electrode during the portions of said off pulses which are after said transients have decayed.

4. A method in accordance with claim 3 in which each impressed rectified current is with a period of applied signals at a nominal 50 Hz or 60 Hz frequency and:

(a) wherein said digital samples are taken at a sample rate which is sufficient to permit digital filtering of alternating currents at the nominal alternating current frequency and harmonics thereof; and (b) wherein said polarized potential is detected by (i) digitally filtering out alternating currents at said nominal frequency to obtain composite samples representing the average potential averaged over each 50 Hz or 60 Hz cycle;

(ii) selecting and summing composite samples to obtain a first sum representing the area under said time varying potential when no off pulse is being detected;

(iii) selecting and summing composite samples representing the area under said time varying potential in the absence of said transients to obtain a second sum;

(iv) subtracting the second sum from the first sum to obtain a difference representing the area of the off pulses;

(v) dividing the difference by the number of composite samples per off pulse which it represents to obtain potential $E_{IR}$, (vi) dividing said first sum by the number of samples it represents to obtain potential $E_{IR}$;

(vii) computing the polarized potential, $E_{OFF}$, by subtracting $E_{IR}$ from $E_{ON}$; and (viii) displaying $E_{OFF}$.

5. A method in accordance with claim 4 wherein said off pulse duration is an integral multiple of the actual period of said nominal 50 Hz or 60 Hz, said off pulse period is an integral multiple of the actual period of said nominal 50 Hz or 60 Hz signal and wherein said sampling and conversion includes taking the same integral number of samples during each actual period of said nominal 50 Hz or 60 Hz signal.

6. A method in accordance with claim 5 wherein said off pulse period is an integral multiple of said off pulse duration.

7. A method in accordance with claim 6 wherein said sampling and conversion includes taking 64 samples during each actual period of said nominal 50 Hz or 60 Hz signal wherein said pulse duration is 16 actual periods of said nominal 50 Hz or 60 Hz signal and wherein said off pulse period is 256 actual periods of said nominal 50 Hz or 60 Hz signal.

8. A method in accordance with claim 4 wherein:

(a) said digital samples are taken over an entire off pulse period;

(b) said digital filtering comprises summing all the samples for each 50 Hz or 60 Hz cycle to form a composite sample for each 50 Hz or 60 Hz cycle; and (c) the composite samples representing $E_{ON}$ are selected by:

(i) discarding the smallest m composite samples, where m is at least the product of the number of 60 Hz or 50 Hz cycles during a pulse period multiplied by said maximum number of impressed current sources which substantially effect a test site along a pipe; and (ii) discarding the largest n samples, where n is at least the product of the integral number of 50 Hz or 60 Hz cycles which occur during said reactive switching transient decay time multiplied by said maximum number of impressed current sources.

9. A method in accordance with claim 8 wherein said second sum representing the area under said time varying potential is obtained by:

(a) summing spaced groups of adjacent composite samples to obtain a sum representing a comb;

(b) repeating step (a) by advancing said groups by an integral number of samples to obtain a further sum representing another comb;

(c) repeating step (b) to obtain a series of sums, each representing a comb; and (d) selecting the largest of the series of sums as representing the area under said time varying potential.

10. A method in accordance with claim 4 wherein said second sum representing the area under said time varying potential is obtained by:

(a) summing spaced groups of adjacent composite samples to obtain a sum representing a comb;

(b) repeating step (a) by advancing said groups by an integral number of samples to obtain a further sum representing another comb;

(c) repeating step (b) to obtain a series of sums, each representing a comb; and (d) selecting the largest of the series of sums as representing the area under said time varying potential.

11. A method in accordance with claim 10 wherein each of said groups of samples is substantially equal to the number of samples during half of an off pulse duration and said groups are spaced by an equal number samples.

12. A method in accordance with claim 11 wherein 256 samples are taken during each off pulse period, the off pulses are 16 sample intervals said groups are groups of eight samples.

13. An apparatus for detecting the polarized potential of a buried pipe which is cathodically protected by current impressed upon the pipe from at least on alternating, rectified source of current, said apparatus comprising:
(a) switching means connected to each said source for periodically pulsing the rectified current to an off state for a off pulse duration which is longer than the time for reactive switching transients to decay and shorter than the time for the polarized potential to vary substantially, said off pulse duration and (the pulse) period being synchronized with said alternating current for varying in proportion to any variations in the period of said alternating current;
(b) analog to digital sampling and conversion means having its input connected between the pipe and a buried electrode at a test site along the pipe for detecting and converting the time varying potential to digital samples for a off pulse period, said conversion means being timed with said alternating current for varying its sample rate in proportion to variations in the period of said alternating current for taking essentially same number of samples during a off pulse period without consequences of variations in said alternating current; and
(c) waveform analysis, data processing means connected to the digital output of said analog to digital sampling and conversion means, for filtering out alternating current signals and harmonics thereof, and for analyzing the resulting waveform to determine the average instantaneous potential, $E_{ON}$, between the pipe and the electrode when no off pulse is present, to determine the average $E_{IR}$ of the sum of the potential drops during each off pulse after the reactive transients have decayed, and for subtracting the average potential drop $E_{IR}$ from $E_{ON}$ and displaying the difference, $E_{OFF}$.

14. An apparatus in accordance with claim 13 wherein said alternating current is with a period of applied signal at a normal 50 Hz or 60 Hz frequency, wherein said off pulse duration is an integral multiple of the actual period of said nominal 50 Hz or 60 Hz, said off pulse period is an integral multiple of the actual period of said nominal 50 Hz or 60 Hz and wherein said sampling and conversion means takes the same integral number of samples during each actual period of said nominal 50 Hz or 60 Hz frequency signal.

15. An apparatus in accordance with claim 14 wherein said off pulse period is an integral multiple of said off pulse duration.

16. An apparatus in accordance with claim 15 wherein said sampling and conversion means takes 64 samples during each actual period of said nominal 50 Hz or 60 Hz frequency, wherein said off pulse duration is 16 actual periods of said nominal 50 Hz or 60 Hz frequency and wherein said off pulse period is 256 actual periods of said nominal 50 Hz or 60 Hz frequency.

* * * * *

UNITED STATES PATENT AND TRADEMARK OFFICE
CERTIFICATE OF CORRECTION

PATENT NO. : 4,823,072
DATED : April 18, 1989
INVENTOR(S) : Walcott, et al.

It is certified that error appears in the above-identified patent and that said Letters Patent is hereby corrected as shown below:

Column 10, Claim 1, line 22 after "rectified protection current" insert -- at --.

Column 10, Claim 1, line 38 change "diving" to -- dividing --.

Column 13, Claim 13, line 14 delete "the pulse".

Column 14, Claim 14, line 12 change "normal" to -- nominal --.

Signed and Sealed this

Fifth Day of September, 1989

Attest:

DONALD J. QUIGG

Attesting Officer

Commissioner of Patents and Trademarks